United States Patent [19]
Brooks et al.

[11] Patent Number: 5,320,957
[45] Date of Patent: *Jun. 14, 1994

[54] METHOD FOR CLONING RESTRICTION MODIFICATION SYSTEM

[75] Inventors: Joan E. Brooks, Beverly; Kimberly A. Howard, Belmont, both of Mass.

[73] Assignee: New England Biolabs, Inc., Beverly, Mass.

[*] Notice: The portion of the term of this patent subsequent to Aug. 11, 2009.

[21] Appl. No.: 928,515

[22] Filed: Aug. 11, 1992

Related U.S. Application Data

[60] Continuation of Ser. No. 797,996, Nov. 26, 1991, which is a division of Ser. No. 453,238, Dec. 14, 1989, Pat. No. 5,137,823, which is a continuation of Ser. No. 872,046, Jun. 6, 1986, abandoned.

[51] Int. Cl.$^5$ .................. C12N 15/55; C12N 9/22
[52] U.S. Cl. .................. 435/172.3; 435/193; 435/199
[58] Field of Search ............ 435/172.3, 193, 199

[56] References Cited

FOREIGN PATENT DOCUMENTS 0105608 4/1984 European Pat. Off. .

OTHER PUBLICATIONS

Makula, et. al. (1980)Nuc. Acids Res 8(14), 3125–3131.
Kiss, et al (1985) Nuc. Acids Res 13(18), 6403–6421.
Bougueleret, et. al. (1984) Nuc. Acids Res 12, 3659–3677.
Greene, et al. (1981) J. Biol. Chem.l256, 2143–2153.
Newman, A. K., et. al. (1981) J. Biol. Chem 256, 2131–2139.
Schoner, et al. (1983) Gene 24, 227–236.
Walder, et al. (1984) J. Biol. Chem 259, 8015–8026.
Suggs, S. V., et al. (1981) Proc. Natl. Acad. Sci., USA 78(1), 6613–6617.
Roberts, et al. (1977) Nature 265, 82–84.
Mann et al., Gene, 3:97–112 (1978).
Walder et al., Proc. Natl. Acad. Sci. USA, 78:1503–1507 (1981).
Gingeras and Brooks, Proc. Natl. Acad. Sci. USA 80:402–406 (1983).
Theriault & Roy, Gene, 19:355–359 (1982).
Blumenthal et al., J. Bacteriol., 164:501–509 (1985).
Szomolanyi et al., Gene, 10:219–225 (1980).
Walder et al., J. Biol. Chem., 258:1235–1241 (1983).
Theriault et al., Nucl. Acids Res., 13 (23):8441–8461 (1985).
O'Connor et al., Gene, 20:219–229 (1982).
Roberts, Nucleic Acids Research, 12S:R167-204 (1984).
Revel, Amer. Soc. of Microbiology, 156–165 (1983).
Revel et al., Annual Review of Genetics, 4:177–192 (1970).
Bachmann, Bacteriol, Rev., 36:525–557 (1972).
Berg et al., DNA Insertions Elements, Plasmids & Episomes, Cold Spring Harbor Laboratories, 205–212 (1977).
Sanger et al., J. Mol. Biol., 162:729–773 (1982).
Streek, Gene, 12:267–275 (1980).
Revel, Virology, 31:688–701 (1967).
Chang & Cohen, J. Bacterial., 134:1141–1146 (1978).
Maniatis et al., In Molecular Cloning, A Laboratory Manual, Cold Springs Harbor Laboratory, pp. 98–103 (1982).
Davis, Medical Microbiology, pp. 854, 219–220, 180 (1980).
Lunnen et al., Gene, 77:11–19 (1989).
Janulaitis et al., Gene: 197–204 (1982).
Wilson et al., Trends in Genetics, 4:314–318 (1988).
Raleigh & Wilson, Proc. Natl. Acad. Sci. USA, 83:9070–9074 (1986).
Southern, J. Mol. Biol., 98:503–517 (1975).
Strickler et al., Analytical Biochemistry, 140:553–566 (1984).
Hunkapillar & Hood, Methods in Enzymology, 91:486–493 (1983).

Primary Examiner—Charles L. Patterson, Jr.
Attorney, Agent, or Firm—Gregory D. Williams; David G. Conlin

[57] ABSTRACT

A two-step method for cloning restriction modification systems is provided which comprises introducing the modification or methylase gene into a host cell and expressing the gene therein to protect the host cell followed by introducing the restriction or endonuclease gene into the host whereby the restriction gene is expressed at lower levels relative to the modification gene. Related methods for producing restriction enzymes is also disclosed as well as clones containing the BamI and DdeI restriction genes.

16 Claims, 7 Drawing Sheets

Tn5 MAPPING OF pDdeM3.0a AND CONSTRUCTION OF pDdeM1.6

M. DdeI IS A CYTOSINE METHYLASE (A)

(B)

pDH2 (pBR322 + 2.2 Kb FRAGMENT FROM pDH1)

METHOD FOR CLONING RESTRICTION MODIFICATION SYSTEM

This is a divisional of copending application(s) Ser. No. 07/797,996 filed on Nov. 26, 1991, which is a divisional of Ser. No. 07/453,238, U.S. Pat. No. 5,137,823 filed Dec. 14, 1989 which is a continuation of Ser. No. 06/872,046 filed Jun. 6, 1986, now abandoned.

BACKGROUND OF THE INVENTION

The present invention relates to a method for cloning restriction-modification systems, to the clones produced thereby, and to methods for producing restriction and-/or modification enzymes from the clones. This invention also relates to clones for the DdeI and BamHI restriction endonucleases and modification methylases, and related methods for the production of these clones and enzymes.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identifyied and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. Close to one hundred different restriction endonucleases have been identified among the many hundreds of bacterial species that have been examined to date.

Bacteria tend to possess at most only a small number restriction endonucleases per species. The endonucleases typically are named according to the bacteria from which they are derived. Thus, the species *Haemophilus aegyptius*, for example synthesizes 3 different restriction endonucleases, named Hae I, Hae II and Hae III. Those enzymes recognize and cleave the sequences (AT)GGCC(AT), PuGCGCPy and GGCC respectively. *Escherichia coli* RY13, on the other hand, synthesizes only one enzyme, EcoR I, which recognizes the sequence GAATTC.

In nature, restriction endonucleases play a protective role in the welfare of the bacterial cell. They enable bacteria to resist infection by foreign DNA molecules like viruses and plasmids that would otherwise destroy or parasitize them. They impart resistance by scanning the lengths of the infecting DNA molecule and cleaving them each time that the recognition sequence occurs. The break-up that takes place disables many of the infecting genes and renders the DNA susceptible to further degradation by non-specific endonucleases.

A second component of bacterial protective systems are the modification methylases. These enzymes are complementary to restriction endonucleases and they provide the means by which bacteria are able to identify their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following this methylation, the recognition sequence is no longer bound or cleaved by the restriction endonuclease. The DNA of a bacterial cell is always fully modified, by virtue of its modification methylase, and it is therefore completely insensitive to the presence of the endogenous restriction endonuclease. It is only unmodified, and therefore identifiably foreign, DNA that is sensitive to restriction endonuclease recognition and attack.

With the advent of genetic engineering technology, it is now possible to clone genes and to produce the proteins and enzymes that they encode in greater quantities than are obtainable by conventional purification techniques. The key to isolating restriction endonuclease clones is to develop a simple and reliable method to identify such clones within complex 'libraries', i.e. populations of clones derived by 'shotgun' procedures, when they occur at frequencies as low as $10^{-4}$ to $10^{-3}$. Preferably, the method should be selective, such that the unwanted majority of clones are destroyed while the rare desirable clones survive.

Type II restriction-modification systems are being cloned with increasing rapidity. The first cloned systems used bacteriophage infection as a means of selectively isolating restriction endonuclease clones (for PstI Walder et al., Proc. Nat. Acad. Sci. 74 1503-1507 (1981), HhaII Mann et al. Gene 3: 97-112 (1981). Since the presence of restriction-modification systems in bacteria enable them to resist infection by bacteriophages, cells that carry cloned restriction modification genes can in principle be selectively isolated as survivors from libraries that have been exposed to phage. This method has been found, however, to have only limited value. Specifically, it has been found that cloned restriction-modification genes do not always manifest sufficient phage resistance to confer selective survival. Another cloning approach involves transferring systems initially characterized as plasmid-borne into E. coli cloning plasmids (EcoRV, Bougueleret et al., Nucl. Acid. Res. 129:3659-3676 1984: PaeR7, Gingeras and Brooks, Proc. Natl. Acad. Sci. USA 80:402-406 1983, Theriault and Roy, 1982; PvuII, Blumenthal et al., J. Bacteriol. 164:501-509 1985. Finally, a growing number of systems are now being cloned by selection for an active methylase gene (BsuRI, Kiss et al., Nucl. Acid. Res. 13:6403-6421 1986; TaqI); since the two genes are often closely linked, both genes are cloned simultaneously. However, the methylase selection does not always yield a complete restriction system (BspRI, Szomolanyi et al., Gene 10:219-225 1980; MspI, Walder et al., J. Biol. Chem. 258:1235-1241 1983). Even attempts to clone larger regions adjacent to the methylase gene can fail to produce an active endonuclease gene.

In some systems the cloning problem may lie in trying to introduce the endonuclease gene into a host not adequately protected by methylation. If the methylase gene and endonuclease gene are introduced on a common DNA fragment, the former gene product must modify the host before the latter gene product cleaves the host genome.

Another obstacle to cloning these systems in *E. coli* was discovered in the process of cloning diverse methylases. Many *E. coli* strains (including those normally used in cloning) have systems that block introduction of DNA containing heterologous cytosine methylation into the cells (Raleigh and Wilson, submitted for publication). Therefore, it is also necessary to carefully consider which *E. coli* strain(s) to use for cloning.

Because purified restriction endonucleases, and to a lesser extent, modification methylases, are useful tools for characterizing and rearranging DNA in the laboratory, there is a commercial incentive to develop methods of obtaining strains of bacteria that synthesize these enzymes in abundance. Such strains would be useful because they would simplify the task of purification as well as providing the means for production in commercially useful amounts.

SUMMARY OF THE INVENTION

In accordance with the present invention, there is provided a novel approach to the production of restriction enzymes and/or their corresponding modification enzymes by cloning genes that encode them and arranging for the genes to be expressed at elevated levels. More specifically, there is provided a novel method of cloning these enzymes, the clones so produced and methods of producing the enzymes themselves which comprises cloning and expressing the methylase gene in an appropriate host in order to adequately protect the host by methylation, and in a second step, cloning and introducing into the host containing the methylase clone the endonuclease gene on a vector which expresses endonuclease at lower levels relative to the methylase gene.

The application of this method to the DdeI and BamHI restriction and modification genes of *Desulfovibrio desulfuricans* and *Bacillus amyloiquefaciens*, respectively, is described in detail, together with the resulting clones that form the basis of a new and useful process for purifying the DdeI and BamHI restriction and modification enzymes.

BRIEF DESCRIPTION OF THE DRAWINGS

FIG. 4A illustrates Southern blot using 3.0 kb HindIII insert from pDdeM3.0a to probe genomic DNA digests. FIG. 4B illustrates the restriction Map of *D. desulfuricans* genome in the region containing the DdeI system and derivative plasmids.

DETAILED DESCRIPTION OF THE INVENTION

Figure 1:
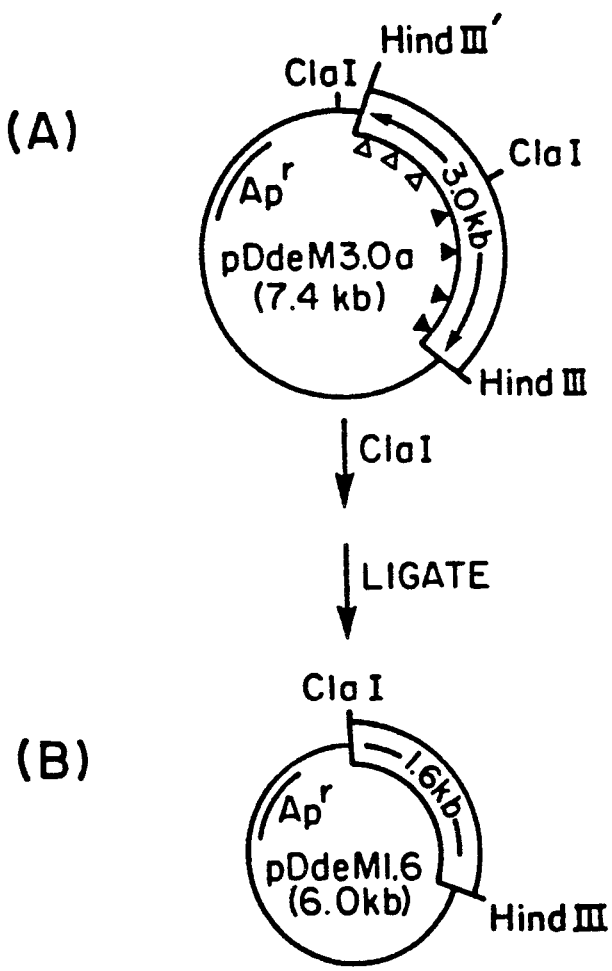
FIG. 1A & B illustrates Tn5 mapping of the pDde3.0a methylase carrying plasmid and construction of pDdeM 1.6, the clone that expresses high levels of DdeI methylase.

The present invention provides a novel approach for cloning restriction-modification systems using a two-step method and harvesting the restriction enzymes produced thereby. This approach takes advantage of the fact that clones and hosts containing clones which contain modification genes will methylate their own DNA within the corresponding restriction gene's recognition sequence if such sequences are present in the clone or host. Such clones will therefore be resistant to digestion in vitro by the corresponding restriction endonuclease. It therefore follows that introduction of the restriction endonuclease gene into hosts containing these clones will result in the selective survival of methylase protected hosts.

In the first step the methylase gene corresponding to the desired restriction gene is cloned and preferably a derivative expressing high levels of methylase constructed. In the second step the restriction gene is then cloned into a host containing the methylase gene and screened for endonuclease activity. Expression of the endonuclease gene occurs in hosts which have been adequately protected by the corresponding methylase gene.

While not wishing to be bound by theory, it is believed that previous cloning systems which entail introduction of the methylase gene and endonuclease gene on a common DNA fragment into a host often fail to produce an active endonuclease gene due to insufficient methylation of the clone and its host which, in turn allows the corresponding endonuclease to cleave the host genome. In accordance with the present invention such problems are overcome by first introducing and expressing or increasing expressing of the methylase gene and then cloning the endonuclease gene on a vector which expresses endonuclease at lower levels relative to the methylase.

The methods described herein by which restriction genes are preferably cloned and expressed include the following steps:

A. Cloning the Methylase Gene

1. The DNA of the bacterial species to be cloned is purified. It has recently been found that viruses also contain restriction-modification systems and therefore may also be used as a source material.

2. The DNA is digested partially or completely with a convenient restriction endonuclease.

3. The resulting fragments are ligated into a cloning vector, such as pBR322, pUC 8, 9, 18 or 19 or pBR328 or a derivative thereof containing e.g., linkers, and the mixture is used to transform an appropriate host cell such as *E. coli* cells.

4. The DNA/cell mixture is plated on antibiotic media selective for transformed cells. After incubation, the transformed cell colonies are combined, suspended and grown to saturation to form a primary cell library.

5. The recombinant plasmids are purified in toto from the primary cell library to make a primary plasmid library.

6. The plasmid library is then digested to completion in vitro with the restriction enzyme whose corresponding methylase gene is sought. Exonuclease and/or phosphatase may also be added to the digestion to enhance the destruction of non-methylase clones.

7. The digested DNA is transformed into *E. coli* and transformed colonies are again obtained by plating on antibiotic plates. Some of these colonies—secondary cell individuals—may be picked and their DNA analyzed for the presence of the methylase gene. The remaining colonies may be scraped together to form a secondary cell library from which a secondary plasmid library may be subsequently prepared.

8. The secondary plasmid library may be redigested with restriction endonuclease (with or without exonuclease or phosphatase) to repeat the selection, leading to the recovery of tertiary cell individuals, tertiary cell libraries and tertiary plasmid libraries.

9. Each round of restriction endonuclease digestion causes selective destruction of non-methylase clones, and results in an increase in the relative frequency of the desired methylase-carrying clones.

10. Surviving colonies among the secondary and tertiary population are picked and analyzed for the presence of the methylase gene.

11. Methylase screening may be performed by four simple tests:

(a) The recombinant plasmid DNA molecule of the clone may be purified and exposed in vitro to the selecting restriction endonuclease to establish that it is resistant to digestion. Provided that the plasmid vector carries several sites for that endonuclease, resistance indicates modification, rather than mutational site loss.

(b) The recombinant plasmid may be digested with the enzyme initially used to fragment the donor bacterial DNA. The fragments present in the clone should be comprehensible, sufficiently large to encode a methylase gene (i.e., over 500 base pairs) and, most important, common to a variety of independently-formed clones: the same fragment or fragments should be present among all the clones.

(c) The total chromosomal DNA of the clone or a second plasmid DNA introduced into the cell or DNA from phage grown on the cell may be purified and exposed to the selective restriction endonuclease. If the clone carries the methylase gene, the bacterial chromosome, plasmid or phage DNA should be partially or fully methylated and should be found to be resistant to digestion.

(d) The cell extract from the clone may be prepared and assayed in vitro for methylase activity. (Methylase protection and radioactive labelling.) Specific methylase activity is often found.

12. The methylase gene is characterized as either a cytosine or adenine methylase to determine the appropriate host for cloning the corresponding endonuclease gene. Alternatively, a battery of hosts may be used to clone the methylase gene and then determine its methylation specificity.

B. Cloning the Endonuclease Gene

1. Since the endonuclease and methylase genes are frequently closely linked, the region surrounding the methylase gene on the genome is mapped, i.e. by Southern blots using the clone containing the methylase gene as a probe and a probe for the endonuclease gene constructed from homogeneous protein. Any inconsistencies in the map between the methylase clone and the bacterial chromosome may signal where a DNA rearrangement has occurred and may in fact indicate the location of the endonuclease gene.

2. Utilizing the restriction map, the DNA of the bacterial species is again digested with a convenient restriction enzyme. Fragments of appropriate size range which hybridize to the probes are purified and ligated into a cloning vector which expresses endonuclease at lower levels relative to methylase. Suitable vectors are preferably those which are compatible with the cloning vector containing the methylase gene. This mixture is then used to transform the host cell carrying the methylase plasmid. While not preferred, the endonuclease gene may be introduced into the cloning vector containing the methylase gene provided that expression of the endonuclease gene is low or tightly controlled by a promoter. The mixture is used to transform the host cell with or without the methylase plasmid. In either case, the DNA/cell mixture is plated on antibiotic media selective for transformed cells.

3. Restriction endonuclease screening may be carried out in three ways:

(a) The cell extract from the clone may be prepared and assayed in vitro for its ability to digest sensitive DNA. Restriction endonuclease activity should be found.

(b) The cells themselves may be tested in vivo for their ability to resist phage infection. Resistance to phage infection indicates the presence of a restriction-modification system.

(c) Transformant colonies can be tested by hybridization for the presence of sequences complimentary to that of the oligonucleotide probe made to the endonuclease gene and/or regions adjacent but not included in the probe of the methylase gene.

Although the above-outlined steps represent the preferred mode for practicing the present invention, it will be apparent to those skilled in the art that the above-described approach can vary in accordance with techniques known in the art.

Clones containing the restriction and modifications genes of DdeI and BamHI have been produced in accordance with the present invention. The source of DNA containing the above genes *Desulfovibrio desulfuricans* (DdeI) (NCIB 83120) and *Bacillus amyloiquefaciens H* BamHI (A sample has been deposited at the American Type Culture Collection - ATCC 53495).

One important factor, which affects the successful cloning of restriction and modification genes is the strain of *E. coli* that is used as the host. Many bacteria have restriction-modification systems, including *E. coli*. The most common system in *E. coli* is the host specific determinant or "Hsd" system, but other systems, notably Pl, and the EcoR-series, also occur (Roberts, R. J., Nucl. Acids Res. 12S:R167–204 (1984)). These systems interfere with cloning because they cause the destruction of the incoming DNA during transformation, resulting in low numbers of transformants and unrepresentative libraries. In general, therefore, in practicing the present invention, the preferred *E. coli* is one in which the restriction systems have been inactivated through mutation or loss. Preferred strains in which these systems have been inactivated or are absent, and which may be used for general cloning purposes, include HB101(hsdR−M−) ATCC 33694, RR1 (hsdR−M−) ATCC 31343, K802 (hsdR−M−) ATCC 33526, K803(hsdR−M−) ATCC 27065 and M294(hsdR−M−) ATCC 33625 and ER1467 (hsdR−M), a sample of which has been deposited at the American Type Culture Collection ATCC 53496.

With particular regard to the cloning of foreign restriction and/or modification genes into *E. coli* there is an additional system which interferes with successful cloning. The system is obscure and is referred to as the "Rgl" system (Revel, H. R., *Bacteriophage T4*, pp. 156–165 American Society of Microbiology (1983) and Revel et al., Annual Review of Genetics 4:177–192 (1970)). More specifically, the *E. coli* Rgl system restricts DNA molecules that bear methylated cytosine residues, and thus destroys the very self-methylated plasmid clones to be isolated. It has recently, been shown that the Rgl system is controlled by a locus that has been designated 'mcrB' (modified cytosine restriction, Raleigh and Wilson, supra). In order to clone such methylase genes, therefore, it is preferred to use *E. coli* hosts that are defective for both the Hsd (general) system and the Rgl (specific) system. A new series of cloning strains has been constructed by inactivating the 'mcrB' locus with Tn10 insertions. One such strain which is preferably used where the methylase gene is a cytosine-type clone is ER1467 which is a derivative strain of JC1552 (Bachman, Bacteriol. Rev. 36:525; 1972) containing a Tn10 insertion in mcrB. Not all cloned methylase genes are susceptible, however. Specifically, those which methylate adenine residues appear to be entirely unaffected by the Rgl system in contrast to those which methylate cytosine residues.

While not wishing to be bound by theory, it is believed that the Rgl system is made up of two components, designated "Rgl A" and "Rgl B". It appears that Rgl B restricts many cytosine-methylase containing DNAs while Rgl A is presently known to restrict only one specificity clone (Hpa II).

In choosing a host for cloning the restriction and/or modification genes of an uncharacterized restriction-modification system, or one that is known to methylate at cytosines, a preferred host is *E. coli* strain that is triply-mutant, i.e., one that lacks the Hsd, Rgl A and Rgl B systems. Such strains include K802. A preferred host for DdeI is ER1467 which is hst $R^-M^-$ and $rglA^+B^-$. If, on the other hand, the modification system is known to be an adenine-methylase type system, the Rgl activity of the host can be ignored. Although rgl does not interfere with adenine methylases, it appears that other yet weakly characterized systems in *E. coli* may work on adenine methylation. The choice of the host thus depends upon the character of the modification gene to be cloned. Table I summarizes the suitability of several strains of *E. coli* for the cloning of several modification genes.

TABLE 1

| Type of Modification Methylase | Restriction-Modification System | Suitable Strains of *E. coli* | | |
|---|---|---|---|---|
| | | K802 (hsdR−, rglA−B−) | RR1 (hsdR−, rglA+B−) | MM294 (hsdR−, rglA+B−) |
| Adenine-Methylase (known or presumed) | EcoR I | | | |
| | Hha II | | | |
| | Hind III | | | |
| | Hinf I | | | |
| | Pst I | suitable | suitable | suitable |
| | Sal I | | | |
| | Taq I | | | |
| Cytosine-Methylase (known or presumed) (Rgl B - sensitive) | Alu I | | | |
| | Ban I | | | |
| | Ban II | | | |
| | Bgl I | | | |
| | Dde I | | | |
| | FnuD II | | | |
| | Hae II | suitable | suitable | suitable |
| | Hae III | | | |
| | HgiA I | | | |
| | Hha I | | | |
| | Msp I | | | |
| | Nla IV | | | |
| | BamH I | suitable | suitable | unsuitable |
| Cytosine-Methylase Rgl A - sensitive) | Hpa II | suitable | unsuitable | unsuitable |

The following examples are given to additionally illustrate embodiments of the present invention as it is presently preferred to practice. It will be understood that these examples are illustrative, and that the invention is not to be considered as restricted thereto except as indicated in the appended claims.

EXAMPLE I

Cloning of the Dde I Restriction-Modification Genes

A. Cloning the Methylase Gene and Characterization of Its Activity

1. DNA Purification:

*D. desulfuricans* DNA was purified by the following method: 5 grams of frozen cells were resuspended in 20 ml of 25% sucrose, 50 mM Tris, pH 8.0. 10 ml of 0.25M EDTA, pH 8.0 plus 6.0 ml of 10 mg/ml lysozyme in 0.25M Tris, pH 8.0, was added. the suspension was left on ice for two hours. Thereafter, 24 ml of Lysis Buffer (1% Triton X-100, 50 mM Tris, pH 8.0, 67 mM EDTA) plus 5 ml 10% SDS were added and mixed, and the cells were allowed to lyse. An equal volume of phenol (equilibrated with 100 mM Tris, pH 8.0) was added and the solution emulsified by shaking. 70 ml of chloroform was then added and shaken for 10 min. The mix was then spun at 10K for 30 min. in a Beckman centrifuge; the top aqueous layer containing the DNA was transferred to a fresh bottle and re-extracted with phenol/chloroform two more times.

The aqueous layer was then dialyzed against four changes 10 mM Tris, 1 mM EDTA, pH 8.0 over 24 hours. The dialyzed DNA solution was treated with 0.1 volume RNAse (10 mg/ml) for 1 hour at 37° C. 5M NaCl solution was added to a final concentration of 0.4M NaCl, and two volumes of ethanol were layered on top of the solution. The DNA was spooled with a glass rod, washed once with 70% ethanol and then dissolved in 15 ml of 10 mM Tris, 1 mM EDTA, pH 8.0. The DNA was stored frozen at −20° C. From 5 grams of cells, 1.5 mg of purified DNA was recovered.

2. Complete Digestion:

The *D. desulfuricans* library was made by incubating 10 ug purified *D. desulfuricans* DNA with 15 units of HindIII in HindIII buffer (10 mM Tris, pH 7.5; 10 mM MgCl$_2$; 50 mM NaCl; 10 mM B-mercaptoethanol) in a 100 ul reaction for 1 hour at 37° C.

3. Ligation 4 ug of the digested DNA was ligated to 2 ug of HindIII-cleaved and dephosphorylated pBR322 (New England Biolabs) in a reaction volume of 100 ul containing 50 mM Tris, pH 7.5, 10 mM MgCl$_2$, 10 mM DTT, 0.5 MM ATP with 1000 units of T4 DNA Ligase (New England Biolabs). Ligation continued at 16° C. for 4 hours. The sample was then chloroform treated and used to transform 200 ul iced competent RR1 cells (in 50 mM CaCl$_2$). The cells were 'heat-shocked' for 2 min. at 42° C.; diluted into 5 ml Luria Broth (L-Broth) and grown to saturation at 37° C.

4. The transformed cells were harvested by centrifugation (4K, 10 min., Beckman centrifuge), resuspended in 250 ul L-Broth and plated on L agar plates with 100 ug/ml Ampicillin, incubated overnight at 37° C. A mixed population of approximately $10^5$ transformants were washed off the plates with 2.5 ml of 10 mM Tris, pH 7.5, 10 mM MgCl$_2$ buffer.

5. This mixture was used to inoculate 500 ml of LB containing 100 ug/1 ml Ampicillin, and incubated overnight at 37° C. The culture was shaken overnight at 37° C. and then the cells reharvested (4K, 5 min.). The cells were resuspended in 10 ml of 25% sucrose, 50 mM Tris, pH 8.0 at room temperature. 5 ml of 0.25M EDTA pH 8.0 and 3 ml of 10 mg/ml of lysozyme. The solution was kept at 4° C. for 1 hour; then 12 ml of Lysis Buffer added and the cell suspension gently mixed. Upon lysis, the lysate was spun at 15K for one hour. The supernatant was decanted through cheesecloth. Solid Cesium Chloride was added (0.93 g/ml) and ethidium bromide to a concentration of 100 ug/ml. Tubes were filled, balanced and spun in a Beckman Ti70 head in a Beckaman ultracentrifuge at 44,000 rpm for 48 hours at 17° C. The ethidium-stained DNA bands were extracted by a syringe and the DNA precipitated in ethanol upon freezing. The plasmid DNA was collected by spinning at 12K for 20 min. After resuspending in 1 ml 10 mM Tris, pH 8.0, 1 mM EDTA, the DNA was phenol extracted once, chloroform extracted once, and then precipitated in 2 volumes of ethanol, dried and resuspended in 100 ul of 10 mM Tris, pH 8.0, 1 mM EDTA buffer.

6. DdeI cleavage:

5 ug of primary plasmid pool was digested with 80 units of DdeI endonuclease for 1 hour in 10 mM Tris, pH 7.5, 10 mM Mg $Cl_2$, 10 mM B-mercaptoethanol, 100 mM NaCl in a 100 ul reaction.

7. Transformation:

10 ul of the reaction mix was used to transform 200 ul of RR1 cells as described above. After the 2 minute heat treatment, the transformation mix was plated immediately on L-agar plus 100 ug/ml ampicillin. Plates were incubated overnight at 37° C. A comparison of DdeI treated and untreated recombinant plasmids revealed a $10^3$ selection. Colonies were inoculated into 10 ml of L-Broth containing ampicillin to prepare a miniculture and was streaked on LB and ampicillin plates.

8. Miniprep Procedure:

Each culture was processed as follows: The 10-ml overnight culture was pelleted at 6K rpm for 5 minutes and resuspended in 1 ml of 25 mM Tris, pH 8.0, 10 mM EDTA, 50 mM Glucose with 1 mg/ml lysozyme. After 10 minutes at room temp., 2 ml of 0.2M NaOH, 1% SDS solution was added; the tubes were mixed and put at 4° C. for 5 minutes 1.5 ml of 3M Sodium Acetate, pH 4.8, was added, mixed, and incubated on ice for 5 minutes. The mixture was centrifuged at 15K rpm for 10 minutes. The supernatant was poured into a centrifuge tube containing 3.0 ml of isopropanol. After 10 minutes at room temp., the tube was spun at 15K rpm for 10 minutes. The pellet was air-dried at room temperature and resuspended in 0.85 ml 10 mM Tris, 1 mM EDTA pH 8.0. 75 ul of 5M NaCl were added and the DNA isopropanol precipitated again at room temperature. After spinning for 1 min. in an eppendorf centrifuge, the pellet was air-dried and resuspended in 50 ul 10 mM Tris, pH 8.0, 1 mM EDTA containing 20 ug/ml RNase.

9. Methylase Gene Clones:

The plasmids mini-preps were subsequently analyzed by first challenging with DdeI and then analysed by HindIII digestion. Among the survivors, two types were resistant to cleavage by DdeI endonuclease. These carried a 3.0 kb HindIII fragment in opposite orientations relative to pBR322. These plasmids were subsequently shown to carry the DdeI modification methylase gene. The two plasmids were designated pDdeM3.0a and pDdeM3.0b, using the standard method of nomenclature described in Gingeras and Brooks, PNAS (USA) 80: 402 (1985). Crude extracts of these clones (see Sec. B-5, infra) did not show any DdeI endonuclease activity.

The position of the methylase gene within the 3.0 kb HindIII fragment was determined by a series of Tn5 mutagenesis experiments (FIG. 1A) (Berg, D. E. (1977) in *DNA Insertions Elements, Plasmids, and Episomes*, Bukhari, A. I., Shapiro, J. A. and Adhya, S. L. Eds., pp. 205-212, Cold Spring Harbor Laboratoires, New York). HB101 (recA) cells carrying the methylase plasmid pDdeM3.0a or pDdeM3.0b were grown overnight at 30° C. in L-broth plus 100 ug/ml ampicillin plus 0.2% maltose. The saturated cultures were diluted 1:100 in 5 ml of LB plus ampicillin plus maltose and grown to a cell density of approximately $10^9$ cells/ml. 1 ml of these cells were mixed with the Tn5-carrying bacteriophage (lambda 467::Tn5 from N. Kleckner via E. Raleigh) at an m.o.i.=0.1. The mixture was incubated at 30° C. for 2 hours. 0.2 ml aliquots were plated on LB plates containing 50 ug/ml kanamycin, 100 ug/ml ampicillin. Plates were incubated at 30° C. for 48 hours.

Colonies were washed off the plates with 5 ml of 25 mM Tris, pH 8.0, 10 mM EDTA, 50 mM glucose and minipreps were prepared as previously described (see sect. 8, miniprep procedure).

The minipreps were used to transform 200 ul iced competent HB101 cells (in 50 mM Ca $Cl_2$). The cells were 'heat-shocked' for 2 min. at 42° C., then diluted into 1 ml L-Broth and incubated for 1 hour. Cells were plated on L-broth plus 50 ug/ml kanamycin, 100 ug/ml ampicillin.

Transformants were screened for the presence of Tn5-containing plasmids by digesting minipreps of the plasmid DNA with HindIII. Plasmids with Tn5 were tested for DdeI methylase activity by challenging the minipreps with DdeI endonuclease.

As shown in FIG. 1A, only Tn5 insertions between ClaI and HindIII sites resulted in the loss of DdeI methylase activity, suggesting that the gene was contained in the region betwen these sites. By making a ClaI deletion of the pDdeM3.0a, a subclone designated pDdeM1.6 was generated that maintains methylase activity, confirming that the methylase gene lies entirely within this 1.6 kb region (FIG. 1B).

Methylase activity of the three M.DdeI clones was compared using an in vivo protection assay and an in vitro $^3$H-methyl incorporation assay as follows:

a. In vitro $^3$H-methyl Incorporation assay (Gingeras and Brooks, supra):

To assay for methylation three mixtures were prepared:

1. 10× Methylation buffer: 1M NaCl, 0.5M Tris, pH 7.5, 0.1M EDTA, and 50 mm B-Mercaptoethanol.

2. Methylation reaction mix: The substrate, pBR322 linearized with EcoRI was prepared as follows: pBR322 was incubated with 20 fold excess of EcoRI in 100 mM NaCl, 10 mM Tris, pH 7.5, 10 mM $MgCl_2$ at a concentrations of 20 ug/ml. After incubating for 1 hour at 37° C., the linearized plasmid was phenol extracted, ethanol precipitated, and the pellet air-dried. The DNA was resuspended in 10 mM Tris, pH 8.0, 1 mM EDTA to a final concentration of 1 mg/ml linearized plasmid. The methylation reaction mix contained 1 ug(=1 ul) of linearized pBR322 plus 2.5 ul 10× methylation buffer, 0.5 ul $^3$H-S-adenosyl-methionine and H2O to 20 ul.

3. Cell extracts were prepared as follows:

A 5 ml culture of the clone to be tested was grown overnight in L-broth plus 100 ug/ml ampicillin at 37° C. Upon saturation, cells were pelleted by centrifugation at 5K rpm for 10 minutes. The pellets were resuspended in 500 ul sonication buffer (10 mM Tris, pH 7.5, 10 mM B-mercaptoethanol). To this mix, 25 ul lysozyme (10 mg/ml) and 50 ul EDTA (100 mM) were added. Samples were frozen, then thawed on ice. These were sonicated using a single 10 second burst. After adding 5 ul of 1M MgCl$_2$, samples were spun in microfuge for 5 minutes.

To assay the cell extracts, 5 ul of the extract was added to the 20 ul methylation reaction mix and incubated for 30 minutes at 37° C. The entire 25 ul reaction was then pipetted on to 3 mm paper demarcated with 1 inch squares. The paper was air-dried, then washed 2 times with 10% T.C.A. (150 ml), then 2 times with 200 ml isopropanol. Paper was air-dried again, then placed in a tube and covered with scintillation fluid (Omniflour, NEN). To detect level of methylation, samples were counted for $^3$H-methyl incorporation.

b. in vivo lambda protection assay

The methylase-containing plasmids pDdeM3.0a, pDdeM3.0b, and pDdeM1.6 were transformed into the strain ER1467 by the transformation procedure previously described. These clones were grown to saturation in L-Broth plus 100 ug/ml ampicillin. After inoculation 1:100 into 10 ml L-broth plus ampicillin, cells were grown to mid-log stage, then pelleted by centrifugation at 5K rpm for 5 minutes. Cell pellets were resuspended in 1 ml of the following phage buffer 10 mM Tris, pH 7.4, 5 mM MgCl$_2$ 0.2M NaCl, 0.1% gel. 100 ul lambda phage ($10^{11}$ phage/ml) was then added, mixed, and incubated at 37° C. for 30 minutes. The mixture was diluted by adding 9 ml phage buffer, then centrifuged again at 5K rpm for 10 minutes. The pellet was resuspended in 10 ml of L-broth plus 100 ug/ml ampicillin and incubated overnight at 37° C.

The phage DNA was prepared in the following manner. The lysed cells were transferred to a centrifuge tube and 3 drops of chloroform added. Samples were vortexed then centrifuged at 10K rpm for 10 minutes. The pellet was discarded and the supernatant was phenol extracted by adding an equal volume of phenol, vortexing, and centrifuging at 5K rpm for 5 minutes. The aqueous layer was then chloroform extracted, vortexed, and re-centrifuged. The top layer was transferred to a fresh tube, to which 2 volumes of ethanol were added to precipitate the DNA. After centrifuging 10K rpm for 20 minutes, the pellet was air-dried and resuspended in 1 ml of 10 mM Tris, pH 8.0, 1 mM EDTA, 20 ug/ml RNase.

Figure 2:
FIG. 2 illustrates the results of an in vivo protection assay for M.DdeI clones.

To test the phage DNA for modification, we mixed 20-40 ul of phage DNA with the following: 5 ul 10 DdeI buffer (1M NaCl, 100 mM Tris, pH 7.5, and 100 mM MgCl$_2$) and 1.5 ul DdeI endonuclease (10,000 units/ml in a reaction volume of 50 ul. The entire sample was analyzed by gel electrophoresis, as shown in FIG. 2.

Both in vitro and in vivo assays revealed a gradation of methylase activity, with pDdeM3.0b having the lowest activity and pDdeM1.6 having the highest; only pDdeM1.6 has enough activity to completely protect lambda phage in vivo. In vitro assays were consistent with these results. pDdeM1.6 was therefore used in later attempts to clone the endonuclease gene (See below).

It is possible to demonstrate that M.DdeI is a cytosine rather than an adenine methylase in the following way: lambda DNA contains overlapping Sau3a (GATC) and DdeI (CTNAG) sites at position 2532: 5'-GATCT-CAG-3' Suggs, S. V., Wallace, R. B., Hirose, T., Kawashima, E. H. and Itakura, K. (1981) PNAS (USA) 78,6613-6617, Sanger, F., Coulson, A. R., Hong, G. F., Hill, D. F. and Petersen, G. B. (1982) J. Moh Biol. 162, 729-773.

Figure 3:
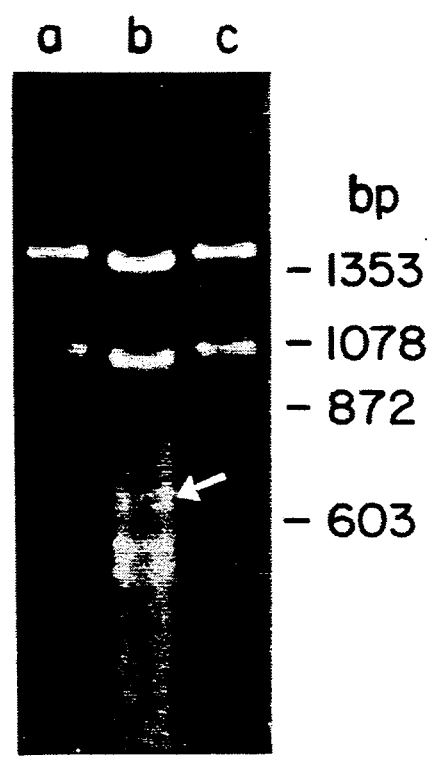
FIG. 3 shows that M.DdeI is a cytosine-type methylase.

Cleavage of lambda DNA with Sau3a results in 165 bp and 487 bp fragments from this region. A 5.0 kb MluI fragment contains the overlapping Sau3a and DdeI sites. This fragment was isolated so that the relevant Sau3a fragments could be better visualized. We treated this lambda fragment with M.DdeI and then challenged with Sau3a. If M.DdeI were an adenine methylase, the modification would occur on the second adenine within this sequence, outside the Sau3a recognition site. Sau3a cleavage would therefore result in the normal 165 bp and 487 bp fragments. If, however, M.DdeI is a cytosine methylase, modification would occur on the cytosine within the Sau3a recognition sequence. Hemi-methylation within the Sau3a site blocks Sau3a cleavage; only single-stranded nicking occurs Streek, R. E. (1980) Gene 12,267. Sau3a a treatment would then result in the appearance of a new 652 bp fragment. As shown in FIG. 3, the new band does in fact appear, indication that M.DdeI is a cytosine methylase.

Realization that M.DdeI is a cytosine methylase helped explain the following phenomenon. The clone that produces the most methylase, which carries pDdeM1.6, was considerably less viable that pDdeM3.0b constructs in our cloning strain RR1. When a culture of RR1 carrying pDdeM1.6 reached stationary phase, it had only 6% the number of viable cells as did a parallel culture of RR1 alone (Table II). It has been recently shown that certain *E. coli* strains have systems that block introduction of DNA containing cytosine methylation (Raleigh et al., in press); the locus responsible for this activity has been designated 'mcrB' (modified cytosine restriction). In RR1, this locus is derived from *E. coli* B and is of different specificity and apparently weaker activity (Raleigh et al., supra, Revel, H. R. (1967), Virology 31, 688-701). A new series of cloning strains has been constructed by inactivating mcrB locus with Tn10 insertions. We introduced our methylase clones into one of these strains, ER1467: comparison of pDdeM3.0a, pDdeM3.0b, pDdeM1.6, and ER1467 alone shows a complete restoration of viability; there was a negligible difference in the number of colony-forming units (c.f.u.) at saturation Table II. Therefore, further cloning and characterization of the DdeI system were done in ER1467.

TABLE II

| VIABILITY OF METHYLASE CLONES IN RR1 vs. ER1467 | | | |
|---|---|---|---|
| HOST | M.DdeI PLASMID | C.F.U./ml | VIABILITY[1] |
| RR1 | — | 4.8 × 10$^8$ | 1.00 |
| RR1 | pDDEM3.0b | 4.1 × 10$^8$ | 0.85 |
| RR1 | pDDEM3.0a | 2.7 × 10$^8$ | 0.56 |
| RR1 | pDDEM1.6 | 0.3 × 10$^8$ | 0.06 |
| ER1467 | — | 6.3 × 10$^8$ | 1.00 |
| ER1467 | pDDEM3.0b | 7.2 × 10$^8$ | 1.14 |
| ER1467 | pDDEM3.0a | 7.0 × 10$^8$ | 1.11 |
| ER1467 | pDDEM1.6 | 5.7 × 10$^8$ | 0.90 |

[1]Viability is defined as the ration of c.f.u./ml s of the test strain to the c.f.u./ml of the host (RR1 or ER1467) alone at saturation.

B. Cloning the Endonuclease Gene

Figure 4:
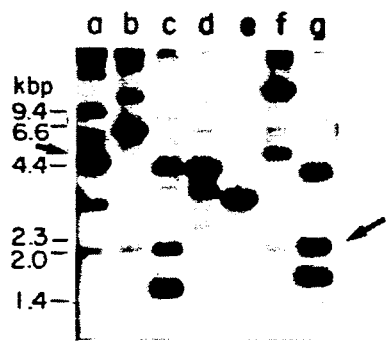
FIG. 4 illustrates Southern Blot Analysis and Restriction Map of DdeI Clones.
Figure 4:
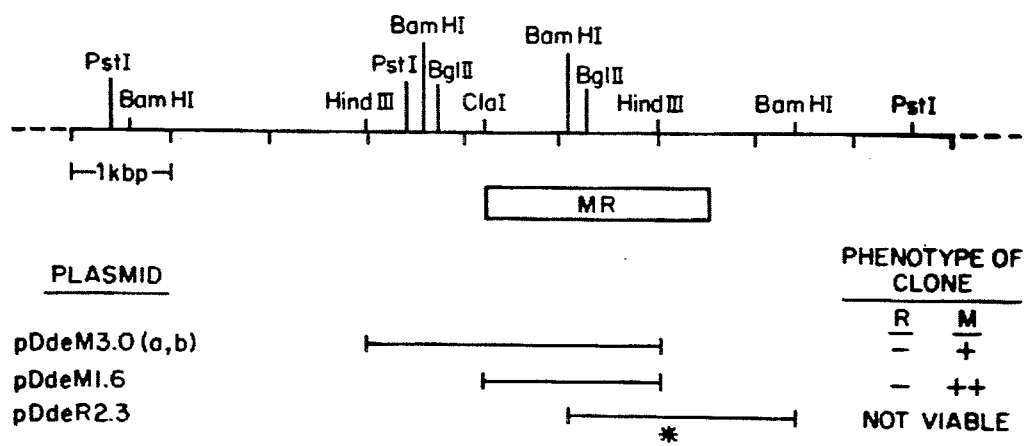

Since endonuclease and methylase genes are frequently closely linked, it seemed reasonable to expect that the R.Dde I gene would lie in a region contiguous with the methylase gene. The region around the methylase gene on the *D. desulfuricans* genome was mapped by Southern blot analysis using the 3.0 kb HindIII fragment from pDdeM3.0a as a probe. Results are shown in FIG. 4A.

An oligonucleotide probe specific for the 5'-terminus of the endonuclease gene had was synthesized.

Step 1: Purifying DdeI endonuclease to homogeneity: DdeI Endonuclease Purification The 23 gram frozen pellet of *D. desulfuricans* was thawed on ice and resuspended in 120 ml of Sonication Buffer (10 mM KPO$_4$, pH 6.9, 10 mM B-mercaptoethanol, 0.1 mM EDTA), 50 mM NaCl. All steps described below were performed at 4° C. Lysozyme was added to a final concentration of 300 ug/ml, and cells were ruptured by sonication. the cell lysate was centrifuged at 10,000×g for 45 min.

The 120 ml supernatant was loaded on a 2.5×15 cm phosphocellulose P11 (Whatman) column equilibrated with Sonication Buffer, 150 mM NaCl. The enzyme was eluted with a linear gradient of 700 ml, from 150 mM to 1M NaCl. The endonuclease eluted approximately 0.5M NaCl. Peak fractions were collected and dialyzed against Sonication Buffer, 50 mM NaCl.

The 170 ml enzyme pool from the phosphocellulose column was loaded on a 1.5×15 cm Heparin Sepharose (Pharmacia) column equilibrated with Sonication Buffer, 25 mM NaCl. A 340 ml gradient from 25 mM to 1M NaCl was used, and the enzyme eluted at approximately 0.5M NaCl. Fractions with endonuclease activity were pooled and dialyzed against HPLC Buffer (20 mM Tris, pH 7.5, 10 mM B-mercaptoethanol), 50 mM KCl.

The 10 ml enzyme pool was passed through a Mono Q column (Pharmacia) and a Polyanion SI column (Pharmacia), then absorbed to a 1×8 cm Mono S column (Pharmacia) at 50 mM KCl. A 53 ml linear gradient was developed from 50 mM to 1M KCl. The endonuclease eluted as a single peak at approximately 0.2M KCl.

A Waters Associates Liquid Chromatograph was used to prepare the sample for protein sequencing in the following manner. DdeI endonuclease samples (15 ug) were subjected to chromatography on a Vyadac C4 214TP54 (5 um, 4.6×300 mm) 300 angstrom pore reverse phase column, developed with a linear gradient of 5% acetonitrile in 0.1% trifluoroacetic acid over 25 minutes at a flow rate of 1 ml/min with detection at 214 nm. Individual peaks were collected manually and lyophilized.

Step 2: Protein Sequencing and Synthesis of the Endonuclease Probe

The sequential degradation of proteins was performed with an Applied Biosystems model 470A gasphase sequenator Strickler, J. E., Hunkapiller, M. W. and Wilson, K. S. (1984) Analytical Biochemistry 140, 553–566. The first 19 phenylthiohydantoins were unambiguously identified by high-performance liquid chromatography on an IBM Cyano (um, 4.5×250 mm) column with slight gradient modifications from those previously described Hunkapiller, M. W. and Hood, L. E. (1983) in *Methods in Enzymology*, Hirs, C. H. W. and Timasheff, S. N. Eds., Vol 91, pp. 486–493, Academic Press, New York.

The protein sequence was used to derive a DNA sequence with minimum degeneracy. This tetradecamer was synthesized using a DNA Synthesis Kit (New England Biolabs) and purified by chromatography on a Water Associates C8 (10 um, 0.5×10 cm) Radial Pak column.

The first 19 amino acids of the endonuclease are Met-Lys-Ala-Ala-Thr-Asp-Gln-Glu-Leu-Arg-Lys-Leu-Ile-Val-Leu-Tyr-Asn-Asn-Val. Using the five amino acids underlined, a mixed tetradecameric probe was prepared with the sequence: 5'-ATG-AAR-GCN-GCN-AC-3' (R, nucleotide A or G;N, nucleotide A,G,C, or T). Southern blots of genomic DNA digests were hybridized with the probe. The endonuclease probe does not hybridize to the 3.0 kb HindIII fragment known to contain the methylase gene.

Southern Hybridizations:
1. Using nick translated fragment

1–2 ug of genomic DNA was digested with 20-fold excess of the following endonucleases: Pst I, Sal I, Bgl II, Bcl I, Hind III, EcoRI, BamHI according to recommended conditions (New England Biolabs). Digests were subjected to agarose gel electrophoresis, and the digested DNA transferred to nitrocellulose paper by the method of Southern (Southern, E. M. (1975) J. Mol. Biol. 98, 503–517).

These nitrocellulose filters were hybridized with the 3.0 kb Hind III fragment from pDdeM3.0a. This fragment was prepared by the method of gel purification as follows: pDdeM3.0a was digested with 20-fold excess of Hind III and subjected to electrophoresis on a gel made with 1% agarose, 0.5 ug/ml ethidium bromide. The 3.0 kb fragment containing the DdeI methylase gene was excised from gel and minced by extrusion through a 21.5 gauge needle, suspended in Tris-Acetate buffer, and subjected to ultracentrifugation at 290,000×g in a type SW 50.1 rotor (Beckman) for 35 min at 4° C. The supernatant was brought to 0.4M NaCl and the DNA was isopropanol precipitated. The DNA was resuspended, phenol extracted twice, ethanol precipitated, and resuspended in 10 mM Tris, 1 mM EDTA, pH 8.0. One ug of this fragment was nick translated by combining 100 pmol alpha$^{32}$P-dATP (New England Nuclear 800 Ci/mmol) with 6 ul of the fragment (1ug) 1 ul of 10× Nick Translation buffer (0.5M Tris, pH 7.2, 0.1M Mg SO$_4$, 1 mM DTT, 500 ug/ml BSA), 1 ul dGTP (1 mM), dTTP (1 mM), dCTP(1 mM) mixture, 1 ul *E. coli* DNA Polymerase I (New England Biolabs), and 1 ul of DNAse I (Sigma) dilution (diluted 3 ul of a 3 mg/ml stock into 10 ml H$_2$O). After incubating for 2 hours at 15° C., 50 ul of 20 mM EDTA and 200 ul of 10 mM Tris, pH8.0, 1 mM EDTA were added. This was phenol extracted once, chloroform extracted once, and then 6 ug of denatured salmon sperm DNA was added. The volume was increased to 1 ml with 10 mM Tris, pH 8.0, 1 mM EDTA. After boiling for 10 min., the nick translated fragment was ready to be added to the nitrocellulose filter.

Before hybridizing the nick translated probe, the nitrocellulose filter was prehybridized in Prehybridization Mix: 3 ml of 50× Denhardt's stock (5 g Ficoll, 5 g polyvinylpyrrolidone, 5 g BSA, H2O to 500 ml), 4.5 ml of 20× SSPE stock (174 g NaCl, 27.6 g NaH2PO4.H20, 7.4 g EDTA; pH adjust to 7.4 with NaOH, H$_2$O to 1 liter), 0.3 ml of 10% SDS, 3 ml of 50% dextran sulfate, 4.2 ml H$_2$O for four hours at room temperature.

To hybridize, the nick translated probe was added to the prehybridized filter (including prehybridization mix) and incubated overnight at 65° C. The hybridized filter was washed two times in 2× SSPE (100 ml) at room temp. for 5 min., and two times in 2× SSPE plus 0.5% SDS at 55° C. for 30 min. The filter was then air-dried and exposed to x-ray film.

2. Using oligonucleotide probe.

1-2 ug of genomic DNA or 0.5-1 ug of plasmid DNA was digested, subjected to gel electrophoresis, and transferred to nitrocellulose as previously described. These filters were hybridized to the oligonucleotide probe in the following manner. 2 ul of the probe (25-50 ug/ml) plus 2.5 ul 10× buffer (0.5M Tris, pH 7.6, 0.1M MgCl$_2$, 50 mM DTT, 1 mM Spermidine, 1 mMEDTA) 15 ul H2O, 5 ul gamma-$^{32}$P.ATP (New England Nuclear, 3000 Ci/mmol), and 0.5 ul Polynucleotide kinase (New England Biolabs or Boehringer Mannheim) were mixed and incubated at 37° C. for 30 minutes. The mixture was then heated to 65° C. for 10 min. 1 ml of 10 mMTris, pH 8.0, 1 mM EDTA was added to the labeled probe. This was added to the prehybridized nitrocellulose filter (as described above) and incubated overnight at room temp.

The hybridized filter was washed 2 times with 2× SSPE (200 ml) at room temp. for 5 min., and two times in 2× SSPE plus 0.5% SDS at 30° C. for 30 min. The filter was then air-dried and exposed to x-ray film.

The Southern blots were used to generate the restriction map represented in FIG. 4B. Two enzyme digests yielded fragments that hybridized to both probes and that were large enough to code for the methylase and/or the endonuclease. Both probes hybridize to a single PstI fragment as shown in lane (a), FIG. 4A, suggesting that both the endonuclease and the methylase genes are located on this 4.8 kb piece of DNA. In addition, both probes hybridize to a 2.3 kb BamHI fragment, as shown in lane (g), FIG. 4A. This fragment includes a portion of the methylase gene and is large enough to encode the entire endonuclease gene.

The endonuclease and methylase genes were introduced separately on compatible plasmids. 2.3 kb BamHI fragments of *D. desulfuricans* DNA were cloned into pACYC184 [Chang and Cohen, J. Bacteriol, 134:1131 (1978) as follows: 50 ug of the *D. desulfuricans* DNA was cut with BamHI and subjected to electrophoresis. Fragments in the appropriate size range were gel purified as previously described; approximately 100 ng of DNA was recovered, and this amount was ligated to BamHI-cut and dephosphorylated pACYC 184 using Calf Intestine Alkaline Phosphatase (Boehringer Man.). This ligation mix was used to transform ER1467 cells carrying the M.DdeI clone pDDEM1.6. Transformants were selected by plating on L-agar plus 100 ug/ml ampicillin, 30 ug/ml chloramphenicol. Plates were incubated overnight at 37° C.

Figure 6:
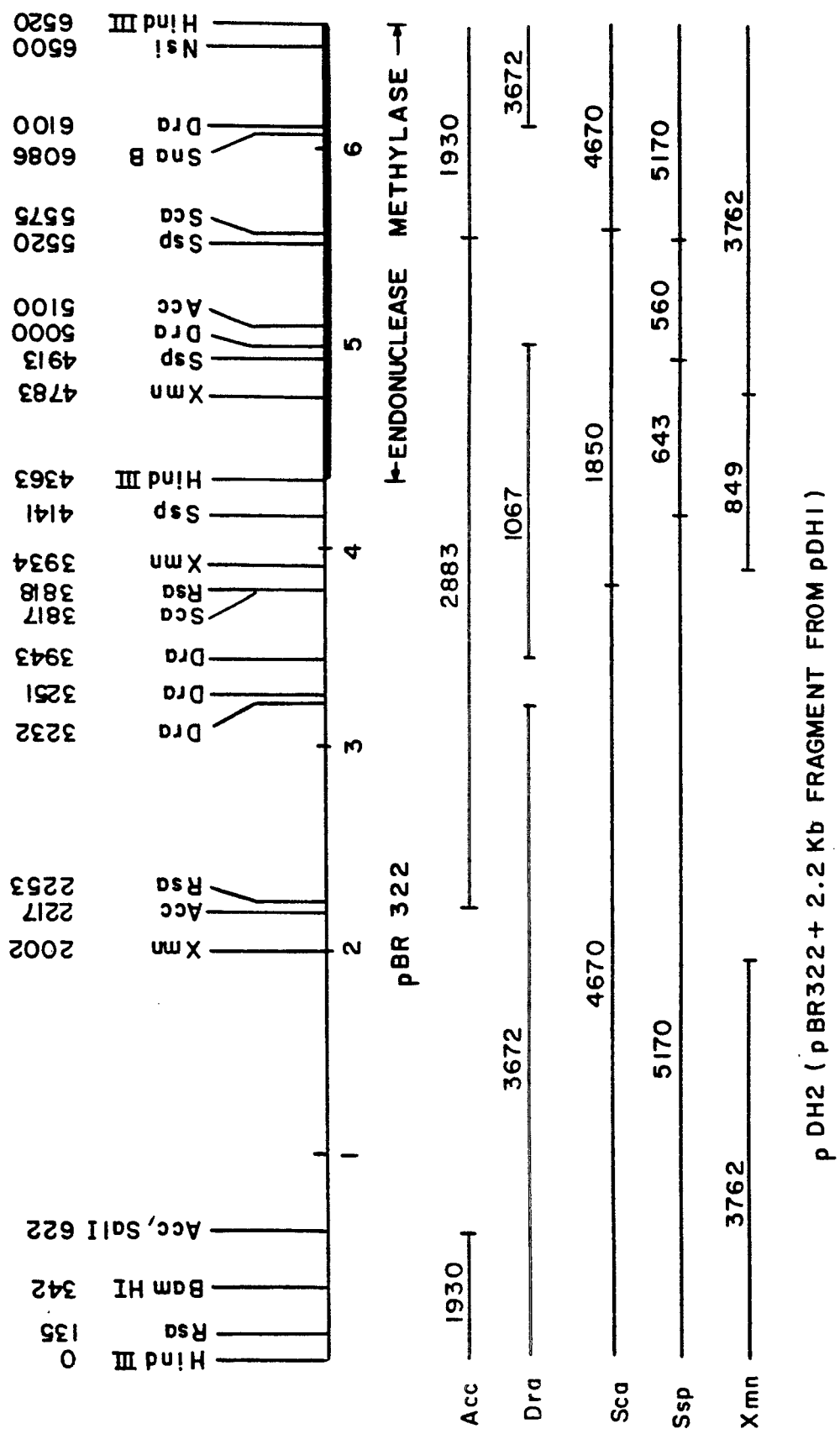
FIG. 6 illustrates mapping of the pDH2 endonuclease carrying clone for BamHI.

5. Restriction Endonuclease Screening:

Fifty transformants were randomly picked with sterile toothpicks into microtiter wells (Nunc), each containing 100 ul L-broth plus 100 ug/ml ampicillin, 30 ug/ml chloramphenicol. After incubating at 37° C. for 6 hours, transformants were replica-plated on six plates containing L-agar, ampicillin, chloramphenicol, and lambda$_{vir.}$ phage dilutions from 10$^4$-10$^8$ phage/plate. After incubating these plates overnight at 37° C., a single transformant restricted phage at a level of approximately 10$^{-1}$. To confirm the presence of active DdeI endonuclease, a crude extract (previously described) of this transformant was prepared. To 1ug pBR322 (=1 ul), 5 ul of 10× dDeI buffer (100 mM Tris, pH 7.5, 100 mM MgCl$_2$ and 1M NaCl), 43 ul H2O, and 1 ul crude extrtact were added and incubated at 37° C. for 30 min, then subjected to agarose gel electrophoresis. DNA from this clone was prepared, and preliminary restriction mapping demonstrated that this 2.3 kb BamHI fragment overlapped the BamHI to Hind III portion of pDDEM1.6 as shown in FIG. 6. Thus the DdeI system is contained within 2.9 kb of *D. desulfuricans* DNA.

EXAMPLE II

Cloning of the BamHI Restriction-Modification Genes

A. Cloning of the BamHI Methylase Gene and Characterization of Its Activity

1. To prepare the DNA of *Bacillus amyloliquefaciens* H, 5 gm of freshly grown cell paste was resuspended in some of 25% sucrose, 50 mmTris pH 8.0. 10 ml of 0.25M EDTA, pH8.0 plus 6.0 ml of 10 mg/ml lysozyme (in 0.25M Tris pH 8.0) was added. The suspension was left on ice for 2 hours. Thereafter 24 ml of lysis buffer (1% Triton X-100, 50 mm Tris pH 8.0 67 mm EDTA) plus 5 ml of 10% SDS was added and mixed, and the cells were allowed to lyse. An equal volume of phenol (equilibrated with 100 mm Tris, pH 8) was added and the solution emulsified by shaking. 70 ml of chloroform was then added and shaken for 10 min. The mix was then spun at 10K for 30 min. in a Beckman centrifuge; the top aqueous layer containing the DNA was transferred to a fresh bottle and re-extracted with phenol-chloroform 2×more.

The upper layer was then dialyzed against 4×1 liter TE (10 mm Tris, 1 mm EDTA pH 8.0) for >24 hrs. After dialysis the DNA was treated with 0.1 volume RNAse (10 ug/ml) for 1 hr at 37° C. 5M NaCl solution was added to a final concentration of 0.4M NaCl with 2 volumes of ethanol layered on top. The DNA was spooled out on a glass rod; washed 1× with 70% EDTA and then redissolved in 15 ml TE, and frozen at −20° C. for storage. Final concentration of DNA=100 ug/ml.

2. Partial digestion: 2 ml of Bam DNA (100 ug/ml) was added to 10 tubes; [200 ug/tube] in HindIII buffer (10 mm Tris pH 7.5; 10 mm MgCl$_2$, 50 mm NaCl, 10 mm mercaptoethanol. The Hind III enzyme was added in a series of 2×dilutions to the tubes; i.e. 40 units in tube 1, 20 units in 2, etc. Digests were carried out at 37° C. for 1 hr; the enzyme was heat killed by incubating the reaction for 15 min. at 72° C. 810 ug of each digest were removed and analyzed by gel electrophoresis. Samples showing partial cleavage were mixed and used:

3. Ligation: 4 ug of Bam DNA digested by Hind III was ligated to 2 ug of alkaline phosphatase treated pBR322 (New England Biolabs) in a reaction volume of 100 ul containing 50mm Tris pH 7.5, 10 mm MgCl$_2$, 10 mm DTT, 0.5 mm ATP with 1000 units of T4DNA Ligase (N.E. Biolabs); ligation continued at 16° C. for 4 hrs. The sample was the chloroform treated, and divided into 10 aliquots; each used to transform 200 ul of iced competent RR1 cells (in 50 mm CaCl$_2$). The cells were 'heat shocked' for 2 min. at 42° C., diluted into 5 ml Luria Broth (L. Broth) and grown to saturation at 37° C.

4. The transformed cells were harvested by centrifugation (4K 10 min.) resuspended in 250 ul L-Broth and plated on L agar plates with 100 ug/ml aapicillin, incubated overnight at 37° C. The transformants were washed off the plates with 2.5 ml 10 mm Tris pH 7.5; 10 mm MgCl$_2$.

5. This mixture was used to inoculate 500 ml of L-Broth containing 100 ug/ml ampicillin. The culture was shaken overnight at 37° C. and then the cells reharvested (4K, 5 min.). The cells were resuspended in 10 ml of 25% sucrose, 50 mm Tris pH8.0 at room temperature 5 ml of 0.25M EDTA pH8 and 3 ml of 10 mg/ml lysozyme in (H$_2$O). The solution was kept at 40° C. for 1 hr; then 12 ml of Lysis Buffer added and the cell suspension gently mixed. Upon lysis the lysate was spun at 15K for 1 hr. The supernatant was decanted through cheesecloth. Solid CsCl was added (0.93 g/ml) and ethidium bromide to a concentration of 100 ug/ml. Tubes were filled, balanced and spun in a Beckman Ti70 head in a Beckman ultracentrifuge at 44,000 rpm for 48 hrs. at 17° C. The ethidium-stained DNA bands were collected through a syringe. The plasmid was precipitated by addition of 2 vol. ethanol and freezing; the plasmid DNA was collected by spinning at 12,000 rpm for 20 min. The DNA after resuspensiion in 1 ml TE buffer, was phenol-extracted 1×; chloroform extracted 1× and then precipitated in 2 vol. ethanol, dried and resuspended in 100 ul TE buffer.

6. Bam challenge: The primary plasmid pool (approx. 100 ug DNA in 100 ul) was digested in 5×100 ul aliquot reactions containing 20 ug of the plasmid DNA in 10 mm Tris pH75, 10 mm MgCl$_2$, 100 mm NaCl; 10 mm B-mercaptoethanol. 100 units of BamHI (N.E. Biolabs) was added to the first tube; 50u to the 2nd, etc., and the tubes were incubated for 1 hr. at 37° C.

7. Transformation: 10 ul from each reaction were used to transform 100 ul of RR1 cell as described above. The transformation mix was plated immediately after heat-treatment for 2 min, and incubated on L agar plus ampicillin overnight at 37° C.

In later experiments it was found that treatment of the restriction reactions with the addition of 2.5 units of exonuclease III (N.E. Biolabs) or with 10 units of alkaline phosphatase (Boehringer) increased the selection by $10^3$ or $10^4$. Approximately 200 colonies were picked from the plates with the lowest numbers of survivors.

8. Each colony was inoculated into 10 ml of L.broth plus ampicillin and also streaked onto an LB plus ampicillin master plate.

Each culture was used to make "mini prep" DNA as follows: the 10 ml culture was harvested [6K for 5 min.] and resuspended in 1 ml of 25 mm Tris, 10 mm EDTA, 50 mm glucose, pH 8 with 1 mg/ml lysozyme. After 10 min. at room temperature, 2 ml of 0.2M NaOH, 1% SDS solution was added; the tube mixed and put at 4° C. for 5 min. 1.5 ml of 3M sodium acetate pH 4.8 was added, mixed and incubated on ice for 5 min. The mixture was spun 15K, for 10 min, the supernatant decanted and added to 3.0 ml isopropanol. After 10 min. at room temp., the tube was spun 15K for 10 min. The pellet was dried and resuspended 0.85 ml TE 75 ul of 5M NaCl were added and the DNA alcohol precipitated once more at room temp. After a 1 min. centrifugation in a Eppendorf centrifuge, the DNA pellet was dried and resuspended in 50 ul TE pH 8.0 containing 20 ug/ml RNASe.

Individual plasmid preparations were then assayed for their Hind III fragment components and resistance to BamHI endonuclease.

Four individual colonies were found that were resistant to BamHI and contained multiple Hind III fragments. Further analysis was done on each of the four. A small amount (10 ml) of cell culture of each clone was grown and the total chromosomal DNA prepared (see section 1). Of these, one contained host DNA resistant to BamHI cleavage and was used for further experiments.

9. Methylase Assays:

In vitro and in vivo assays of BamHI extracts were done as described in Example I except for the in vitro assay the substrate used was ligated BamHI linkers (dpCGGATCCG)) (N.E. Biolabs) that were prepared as follows:

1 O.D. unit of BamHI linkers was ligated in a 100 ul reaction containing with 1000 units T4 DNA Ligase (N.E. Biolabs) 50 mm Tris, pH 8; 20 mm DTT, 2 mm ATP, 10 mm MgCl$_2$ 50 g/ml Bovine Serum Albumin (Pentax), overnight at room temp. The reaction was then heated 10 min. 70° C. to inactivate. 0.005 OD units of linker were added to each methylase reaction; the reaction was carried out with [$^3$H] - S-adenosylmethionine.

In vivo Assays: were carrried out using lambda phage as described in Example I.

The methylase clone was also assayed for endonuclease activity [endonuclease assay of crude extracts were performed as in Example I except 1 ug of pBR322 linearized with 10 units of PstI endonuclease (N.E. Biolabs) was used as a substrate.] No activity was detected.

B. Cloning the Endonuclease Gene

Figure 5:
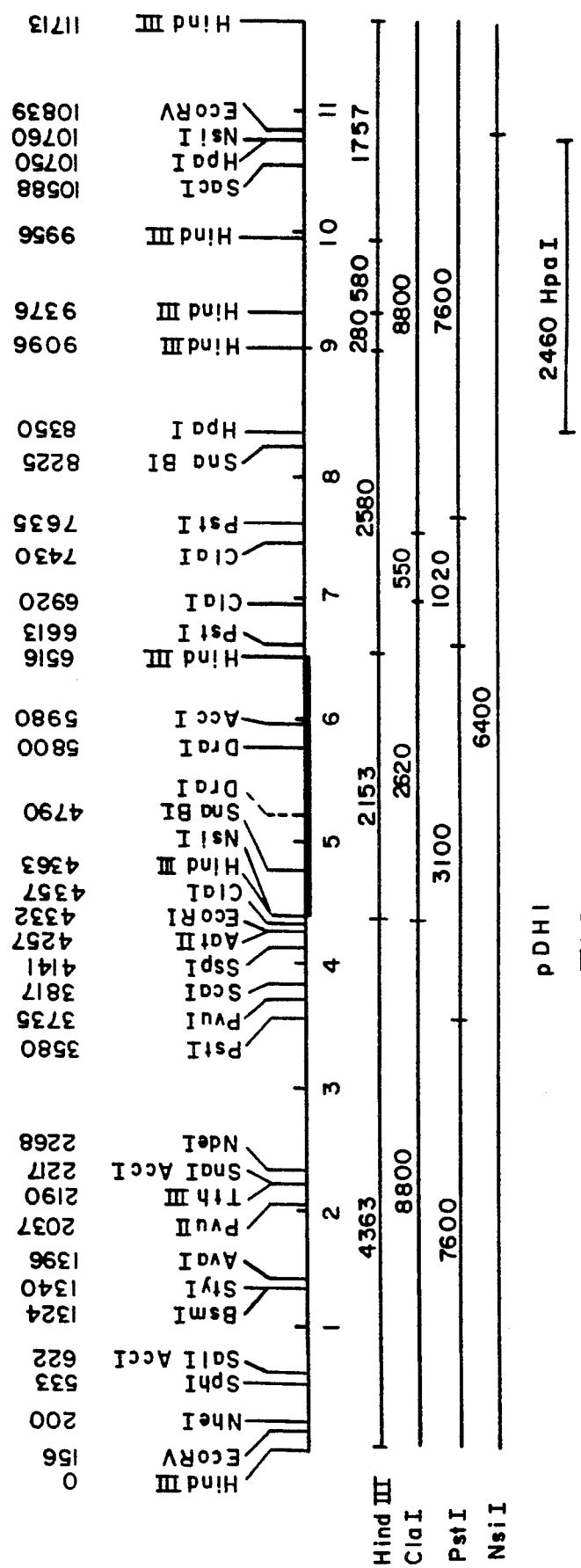
FIG. 5 illustrates mapping of the methlase carrying plasmid for BamHI.

1. Mapping the methylase plasmid:

The order of Hind III fragments were assessed by a series of double digests with restriction endonuclease done under manufacturer's recommended conditions [See FIG. 5].

Additionally, the oligonucleotide probe made from sequence deduced from homogeneous BamHI endonuclease [Analogous to Dde probe—see Example I] was used to order the Hind III fragements in the following manner: 150 ul reaction containing 15 ug of the Bam methylase plasmid in 10 mm Tris pH 7.5, 10 mm MgCl$_2$, 50 mm Nacl was mixed and put in 9 tubes, the first contained 30 ul. 2 units of Hind III endonuclease [N.E. Biolabs] was added to the first tube and one half the volume transferred to the second, etc. so as to accomplish a serial dilution. After 1 hr. the reactions (incubated at 37° C.) were terminated and the digests subjected to electrophoresis on a 0.7% agarose gel. The electrophoresed material was then transferred to a nitrocellulose filter as described in Example I and this used to hybridize with the oligonucleotide probe, which had been made radioactive by treatment with gamma$^{32}$P ATP [New England Nuclear] and T4 polynucleotide kinase [N.E. Biolabs], as described in Example I. This led to finding a 2.2 kb fragment that hybridized to the probe.

2. Mapping and subcloning the methylase gene.

The plasmid containing the methylase gene (designated pDH1) was transformed by CaCl$_2$ treatment into HB101 cells. Plasmid DNA was purified through CsCl gradients as detailed in Section 5.

a) HB101 cells containing pDH1 were infected by lambda467::Tn5 so as to map the methylase function by transposon mutagenesis. Details of this method are given in Example I.

b) The methylase gene appeared to be located on a 2.2 kb Hind III fragment. 100 ug of pDH1 DNA was digested to completion with Hind III and then run out on a preparative 0.7% agarose gel. The 2.2 kb fragment was visualized with longwave UV, excised with a scalpel and electroeluted in an IBI model UEA analytical electroelution apparatus, following manufacturer's instructions. The fragment was precipitated in 2 vol. ethanol, resuspended in 300 ul TE, phenol extracted, chloroform extracted and reprecipited with ethanol plus 0.2M LiCl. The DNA fragment was then resuspended in 100 ul TE and frozen away at −20° C.

c) 2 ug of this fragment was ligated to 0.1 ug of pBR322-Hind III (alkaline phosphatase treated) or 0.1 ug of pUC19-Hind III that had been alkaline phosphatased and the ligation incubated overnight at room temp. The ligation mix (see Section A-3 for details of ligation) was chloroform extracted 1×, and then used to transform competent HB101 cells. Transformants were "mini prepared" and the plasmids tested for methylase activity (Section A-9). Constructs containing the 2.2 kb fragment both in pBR 322 and pUC 19 were Bam methylase producers. These plasmids were designated pDH2 and pDH3 respectively.

d) pDH2 was mapped by standard means and the endonuclease probe also mapped onto the fragment [FIG. 6]. A convenient XmnI site was located approx 450 bp upstream from one Hind III site, close to where the oligonucleotide probe was hybridizing.

10 ug purified 2.2 kb fragment was digested extensively with XmnI endonuclease and the reaction mix phenol extracted, chloroform extracted, ethanol precipitated and resuspended. 5 ug of this DNA was ligated to 0.5 ug pUC8 which had been doubly digested with Hind III and SmaI. The ligation mix was used to transform competent K802 cells. Individual transformants were "mini prepped", to look at their plasmid structure and also the clones tested (in vivo) for Bam methylase activity. One was found having the 1.75 kb HindIII-Xmn fragment and methylase activity (Others having the 0.45 kb fragment were kept for endonuclease probes—they had no Bam methylase activity activity). This shortened construct which was still Bam methylase positive was designated pDH5.

e) Mapping the endonuclease gene onto the Bam chromosome.

Purified *Bacillus amyloiquefaciens* DNA was digested with a series of restriction endonucleases under standard conditions and the digests run out on 0.5% agarose gels. The DNA was transferred to nitrocellulose filters as detailed in Example I. The Southern blot transfers were then hybridized in parallel to kinased Bam oligonucleotide probe [sequence: 5'TCC(T)TTC(T)TCG(TCA)ACC(T)TCCAT3'] and nick translated purified 2.2 kb fragment [nick translation procedure described in Example I].

Figure 7:
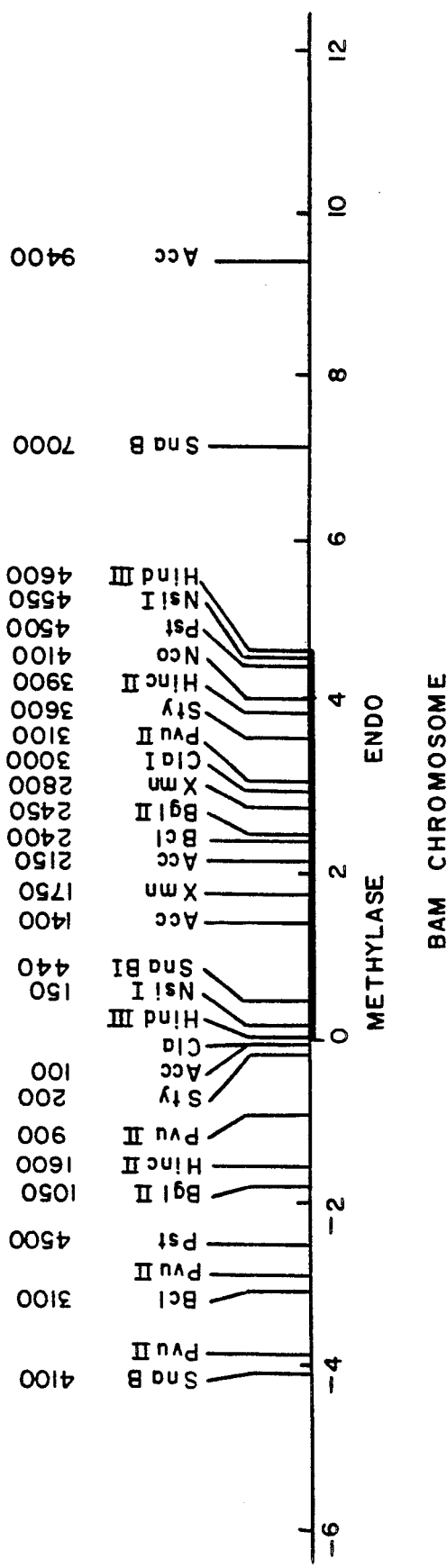
FIG. 7 illustrates the Bam chromosome.

Although the oligo probe hybridization and washes were carried out with less stringency and therefore more non specific hybridization occurred, it was clear both moieties were hybridizing to the same region of the Bam chromosome (FIG. 7). Specifically, both probes hybridized to a 4.5 kb Hind III fragment on the Bam chromosome.

3. Finding the Endonuclease gene 100 ug of Purified Bam DNA was digested to completion with 200 units of Hind III endonuclease. The DNA was run out on a preparative 0.5% agarose gel excised and electroeluted as described above.

10 ug of the purified 4.5 kb fragments were ligated to 1 ug of pACYC 184 vector that had been Hind III digested and treated with alkaline phosphatase. The ligation mix was diluted from 100 ul to 300 ul after chloroform treatment. 100 ul was used to transform competent K802 cells that had previously been transformed with pDH5.

Transformants that were $Amp^R Cam^R$ were selected. 350 of these were picked by toothpick into sterile microtitre dishes [Nunc] containing 100 l L. Broth+Amp+Cam (chloramphenicol; 30 ug/ml final conc.) and grown at 37° C. overnight. Next day the colonies were stamped onto LB+Amp+Cam plates using a multiprong inoculating device and these were incubated over night at 37° C.; 50 colonies/plate.

Testing for endonuclease activity: To each of the 7 master plates 5 ml of Sonication buffer (100 mm Tris pH8, 10 mm mercaptoethanol) was added and the colonies washed off the surface of the plate. The cell suspension was spun 5K for 10 min. to harvest the cells and they were resuspended in 0.5 ml Sonication buffer. The cells were sonicated for 15 sec. with the microtip, after having been treated with 25 ul of lysozyme (10 mg/ml) and 50 ul of 0.1M EDTA pH7.0 and frozen and thawed. The cell debris from the sonicate was removed, after addition of 10 ul of 1M $MgCl_2$, by low speed centrifugation (5 min. in Eppendorf). 1 ul of each pooled extract was used to digest 1 ug of pBR322 DNA linearized by the addition of 10 ul of PstI to the reaction mix (10 mm, Tris pH8, 10 mm $MgCl_2$, 100 mm NaCl). After resolution of the digests on agarose gels, something promising was seen on plate #5. Therefore cells from each colony were inoculated into 5 ml of LB+Amp+Cam and grown over night, each individually harvested and tested for Bam HI endonuclease activity.

In addition, colonies were checked for phage restriction [See Example I]. One colony was found that had Bam endonuclease activity.

We claim:

1. A method of cloning a restriction-modification system which comprises:
   (a) introducing a modification gene corresponding to the restriction-modification system to be cloned into a cloning vector and expressing said gene in an appropriate host cell, wherein said expression of the modification gene is at levels sufficiently high to protect the host cell DNA from degradation by the restriction-modification system's restriction endonuclease; and
   (b) subsequently introducing a restriction gene corresponding to the restriction-modification system to be cloned into the host cell containing the expressed modification gene.

2. The method of claim 1, wherein introduction of the modification gene into the cloning vector and expression thereof in an appropriate host cell comprises the steps of:
   (a) purifying DNA from a source containing the restriction-modification system to be cloned;
   (b) at least partially digesting the purified DNA to form DNA fragments;
   (c) ligating the fragments into the cloning vector;
   (d) transforming the host cell with the cloning vector of step (c) to form a library;
   (e) screening the library for clones containing the modification gene; and
   (f) culturing the host cells containing the clones of step (e).

3. The method of claim 2, wherein the source of DNA is selected from bacteria or virus containing the restriction-modification system.

4. The method of claim 2, wherein the cloning vector is a plasmid or viral DNA molecule.

5. The method of claim 4, wherein the plasmid is pBR322, pUC8, pUC9, pUC18, or pUC19.

6. The method of claim 5, wherein introduction of said restriction gene into said host cell comprises introducing the restriction gene into a second plasmid which is compatible with the plasmid containing the modification gene and transforming the host cell with said second plasmid.

7. The method of claim 5, wherein introduction of said restriction gene into said host cell comprises introducing the restriction gene into the plasmid containing the modification gene.

8. The method of claim 4, wherein the host cell is selected from the group of ER1467, K802, HB101, RR1, K803 AND MM294.

9. A clone produced in accordance with the method of claim 1, wherein said clone, in the absence of the earlier expressed modification gene, is susceptible to DNA cleavage by the restriction-modification system's restriction endonuclease.

10. A method of producing a restriction enzyme comprising the steps of:
  (a) purifying DNA from a source containing a restriction-modification system to be cloned;
  (b) at least partially digesting the purified DNA to form DNA fragments;
  (c) ligating the fragments into a cloning vector;
  (d) transforming an appropriate host cell, with the cloning vector of step (c) to form a library;
  (e) screening the library for clones containing a modification gene corresponding to the restriction-modification system;
  (f) expressing the modification gene at levels sufficiently high to protect the host cell DNA from degradation by the restriction enzyme to be produced;
  (g) subsequently introducing a restriction gene corresponding to the restriction-modification system into the host cell containing the expressed modification gene;
  (h) culturing the host cells of step (g); and
  (i) recovering the restriction enzyme from the culture.

11. The method of claim 10, wherein the source of DNA is selected from bacteria or virus containing the restriction-modification system.

12. The method of claim 10, wherein the cloning vector is a plasmid or viral DNA molecule.

13. The method of claim 12, wherein the plasmid is pBR322, pUC8, pUC9, pUC18, or pUC19.

14. The method of claim 13, wherein introduction of said restriction gene into said host cell comprises introducing the restriction gene into a second plasmid which is compatible with the plasmid containing the modification gene and transforming the host cell with said second plasmid.

15. The method of claim 13, wherein introduction of said restriction gene into said host cell comprises introducing the restriction gene into the plasmid containing the modification gene.

16. The method of claim 13, wherein the host cell is selected from the group of ER1467, K802, HB101, RR1, K803 and MM294.

* * * * *

UNITED STATES PATENT AND TRADEMARK OFFICE
CERTIFICATE OF CORRECTION

PATENT NO. : 5,320,957
DATED : June 14, 1994
INVENTOR(S) : Brooks, et al

Page 1 of 3

It is certified that error appears in the above-indentified patent and that said Letters Patent is hereby corrected as shown below:

Column 3, line 42, replace "in vivo" with --*in vivo*--

Column 4, line 1, replace "in vitro" with --*in vitro*--

Column 4, line 48, replace "in toto" with --*in toto*--

Column 4, line 52, replace "in vitro" with --*in vitro*--

Column 5, line 11, replace "in vitro" with --*in vitro*--

Column 5, line 33, replace "in vitro" with --*in vitro*--.

Column 6, line 6, replace "in vitro" with --*in vitro*--

Column 6, line 9, replace "in vivo" with --*in vivo*--

Column 6, lines 66-67, replace "modified cytosine restriction" with
--m̲odified c̲ytosine r̲estriction--

Column 6, line 67, replace "supra" with --*supra*--

Column 7, line 41 (in Table 1), replace "rglA+B-)" with --rglA+B+)-- (second occurrence)

Column 7, line 53, replace "Hae II    suitable    suitable    suitable" with
--Hae II    suitable    suitable    unsuitable--

UNITED STATES PATENT AND TRADEMARK OFFICE
CERTIFICATE OF CORRECTION

PATENT NO. : 5,320,957
DATED : June 14, 1994
INVENTOR(S) : Brooks, et al

It is certified that error appears in the above-indentified patent and that said Letters Patent is hereby corrected as shown below:

Column 7, line 60, replace "Rgl A-" with --(Rgl A- --

Column 8, line 61, replace "100 ug/l ml" with --100 ug/ml--

Column 9, line 63, replace "infra" with --*infra* --.

Column 10, line 38, replace "in vivo" with --*in vivo* --

Column 10, lines 38-39, replace "in vitro" with --*in vitro* --

Column 10, line 40, replace "In vitro" with --*In vitro* --

Column 10, line 41, replace "supra" with --*supra* --

Column 11, line 13, replace "in vivo" with --*in vivo* --

Column 11, line 52, replace "in vitro and in vivo" with --*in vitro* and *in vivo* --

Column 11, line 56, replace "in vitro. In vitro" with --*in vitro*. *In vitro* --

Column 12, line 32, replace "modified cytosine restriction" with --m̲odified c̲ytosine r̲estriction--

Column 14, lines 1-2, replace "Met-Lys-Ala-Ala-Thr" with --Met-Lys-Ala-Ala-Thr--

UNITED STATES PATENT AND TRADEMARK OFFICE
CERTIFICATE OF CORRECTION

PATENT NO. : 5,320,957
DATED : June 14, 1994
INVENTOR(S) : Brooks, et al

It is certified that error appears in the above-indentified patent and that said Letters Patent is hereby corrected as shown below:

Column 15, line 8, replace "32P.ATP" with --32P-ATP--

Column 15, line 36, replac e"[Chang" with --(Chang--

Column 18, line 1, replace "In vitro and in vivo" with --*In vitro* and *in vivo* --

Column 18, line 2, replace "in vitro" with --*in vitro* --

Column 19, line 29, replace "in vivo" with --*in vivo* --

Signed and Sealed this

Twenty-fifth Day of October, 1994

BRUCE LEHMAN

Attest:

Attesting Officer

Commissioner of Patents and Trademarks

UNITED STATES PATENT AND TRADEMARK OFFICE
CERTIFICATE OF CORRECTION

PATENT NO. : 5,320,957
DATED : June 14, 1994
INVENTOR(S) : Brooks, et al.

It is certified that error appears in the above-indentified patent and that said Letters Patent is hereby corrected as shown below:

On title page, item [54] and col. 1, lines 1-3, should read as follows:
"METHOD FOR CLONING RESTRICTION MODIFICATION SYSTEM" with --METHOD FOR CLONING RESTRICTION MODIFICATION SYSTEMS--

Column 1, line 40, after "number" insert --of--

Column 2, line 29, replace "(1981)." with --(1981))--

Column 2, line 40, replace "E. coli" with --*E. coli*--.

Column 2, line 53, replace "1983)." with --(1983))--

Column 3, line 31, replace "amyloiquefaciens" with --amyloliquefaciens"

Column 3, line 52, replace "methlase" with --methylase--.

Column 3, line 56, replace "Bam" with --*Bacillus amyloliqufacies* H--

Column 6, line 28, replace "*amyloiquefacies*" with --*amyloliquefaciens*--

Column 6, line 64, replace "It has recently, been" with --It has recently been--

Column 7, line 30, replace "rgl" with --Rgl--

Column 8, line12, replace ", was added. the" with --, was added. The--

Column 9, line 47, replace "eppendorf" with --Eppendorf--.

Column 10, line 1, replace "Laboratoires" with --Laboratories--

Column 10, line 58, replace "H20" with --$H_2O$--.

Page 1 of 6

UNITED STATES PATENT AND TRADEMARK OFFICE
CERTIFICATE OF CORRECTION

PATENT NO. : 5,320,957

DATED : June 14, 1994

INVENTOR(S) : Brooks, et al.

It is certified that error appears in the above-indentified patent and that said Letters Patent is hereby corrected as shown below:

Column 11, line 6, replace "onto" with --onto Whatman--

Column 11, line 8, replace "T.C.A." with --TCA--

Column 11, line 23, replace "0.1% gel." with --0.1% gelatin--

Column 11, line 47, replace "(10,000" with --10,000--

Column 11, line 62, replace "Sau3a" with --Sau3A--

Column 11, line 67, replace "J. Moh Biol." with --*J. Mol. Biol.*--

Column 12, line 1, replace "Sau3a" with --Sau3A--

Column 12, line 3, replace "Sau3a" with --Sau3A--

Column 12, line 5, replace "Sau3a" with --Sau3A--

Column 12, line 7, replace "Sau3a" with --Sau3A--

Column 12, line 9, in both instances, replace "Sau3a" with --Sau3A--

Column 12, line 13, replace "Sau3a" with --Sau3A--

Column 12, line 14, in both instances, replace "Sau3a" with --Sau3A--

Column 12, line 16, replace "Gene 12,267. Sau3a" with --*Gene* 12,267. Sau3A--

Column 12, line 34, replace "et al., supra" with --et al., *supra* --

Column 12, line 35, replace "Virology" with --*Virology*--

Column 12, lines 50 and 54, replace "pDDEM3.0b" with --pDdeM3.0b--.

UNITED STATES PATENT AND TRADEMARK OFFICE
CERTIFICATE OF CORRECTION

PATENT NO. : 5,320,957

DATED : June 14, 1994

INVENTOR(S) : Brooks, et al.

It is certified that error appears in the above-indentified patent and that said Letters Patent is hereby corrected as shown below:

Column 12, lines 51 and 55, replace "pDDEM3.0a" with --pDdeM3.0a--

Column 12, lines 52 and 56, replace "pDDEM1.6" with --pDdeM1.6--

Column 12, the caption under Table II, replace "ration of c.f.u./ml s" with --ratio of c.f.u./ml--

Column 13, line 12, replace "sonication. the" with --sonication. The--

Column 13, line 54, replace "Analytical Biochemistry" with --*Analytical Biochemistry*--

Column 13, line 57, replace "Cyano (um, 4.5 X 250 mm)" with --Cyano (5 um, 4.5 X 250 mm)--

Column 14, lines 19-20, replace "J. Mol. Biol." with --*J. Mol. Biol.*--

Column 14, line 53, after "hybridizing" insert --to--.

Column 14, line 56, replace "H20" with --$H_2O$--

Column 14, line 57, replace "NaH2P04H20" with --$NaH_2O$ $P0_4$ $H_2O$--

Column 15, line 7, replace "1mMEDTA" with --1 mM EDTA--

Column 15, line 13, replace "mMTris" with --mM Tris--

Column 15, line 37, replace "(1978)" with --(1978)]--

Column 15, line 42, replace "pACYC 184" with --pACYC184--

Column 15, line 45, replace "pDDEM1.6" with --pDdeM1.6--

Column 15, line 62, replace "dDel" with --DdeI--

UNITED STATES PATENT AND TRADEMARK OFFICE
CERTIFICATE OF CORRECTION

PATENT NO. : 5,320,957

DATED : June 14, 1994

INVENTOR(S) : Brooks, et al.

It is certified that error appears in the above-indentified patent and that said Letters Patent is hereby corrected as shown below:

Column 15, line 63, replace "H20" with --$H_2O$--.

Column 16, line 1, replace "pDDEM1.6" with --pDdeM1.6--

Column 16, line 12, replace "50 mmTris" with --50 mM Tris--

Column 16, line 16, replace "50 mm" and "67 mm" with --50 mM-- and --67 mM--

Column 16, line 19, replace "100 mm" with --100 mM--

Column 16, line 27, replace "10 mm" and "1 mm" with --10 mM-- and --1 mM--

Column 16, line 38, replace "10 mm", "10 mm" and "50 mm" with --10 mM--, --10 mM-- and --50 mM--

Column 16, line 49, replace "50 mm" and "10 mm" with --50 mM-- and --10 mM--

Column 16, line 50, replace "0.5 mm" and T4DNA" with --0.5 mM-- and --T4 DNA--

Column 16, line 52, replace "the chloroform" with --then chloroform--

Column 16, line 54, replace "50 mm" with --50 mM--

Column 16, line 60, replace "aapicillin" with --ampicillin--

Column 16, lines 62-63, replace "10 mm" and "10 mm" with --10 mM-- and --10 mM--

Column 16, last line, replace "50 mm" with --50 mM--

Column 17, line 21, replace "pH75" with --pH7.5--

Column 17, line 21, replace "10 mm", "100 mm" and "10 mm" with --10 mM--, --100 mM-- and --10 mM--

UNITED STATES PATENT AND TRADEMARK OFFICE
CERTIFICATE OF CORRECTION

PATENT NO. : 5,320,957
DATED : June 14, 1994
INVENTOR(S) : Brooks, et al.

It is certified that error appears in the above-indentified patent and that said Letters Patent is hereby corrected as shown below:

Column 17, line 23, replace "50u" with --50 units--

Column 17, line 36, replace "L.broth" with --L broth--

Column 17, lines 41-42, replace "25mm", "10mm" and "50mm" with --25mM--, --10mM-- and --50mM--.

Column 17, line 50, replace "TE 75" with --TE; 75--

Column 17, line 56, replace "RNASe" with --RNAse--

Column 18, line 4, replace "(dpCGGATCCG))" with --(dpCGGATCCG)--

Column 18, line 8, replace "50 mm", "20 mm" and "2 mm" with --50 mM--, --20 mM-- and --2 mM--

Column 18, line 9, replace "10 mm" with --10 mM--

Column 18, line 15, replace "In vivo" with --*In vivo*--

Column 18, line 33, replace "fragements" with --fragments--

Column 18, line 35, replace "10 mm" and "10 mm" with --10 mM-- and --10 mM--

Column 18, line 36, replace "50 mm" with --50 mM--

Column 19, line 1, replace "reprecipited" with --reprecipitated--

Column 19, line 33, replace "methylase activity activity" with --methylase activity--

Column 19, line 38, replace "*amyloiquefaciens*" with --*amyliloquifaciens*--

Column 19, line 56, replace "Purified" with --purified--

UNITED STATES PATENT AND TRADEMARK OFFICE
CERTIFICATE OF CORRECTION

PATENT NO. : 5,320,957
DATED : June 14, 1994
INVENTOR(S) : Brooks, et al.

It is certified that error appears in the above-indentified patent and that said Letters Patent is hereby corrected as shown below:

Column 20, line 1, replace "100 I L. Broth + Amp- + Cam" with
--100 ul L Broth + Amp (100 ul/ml final conc) + Cam--

Column 20, line 20, replace "10 mm" with --10 mM--

Column 20, line 21, replace "10 mm" and "100 mm" with --10 mM-- and --100 mM--

Signed and Sealed this

Thirty-first Day of January, 1995

Attest:

BRUCE LEHMAN

*Attesting Officer*  Commissioner of Patents and Trademarks